US006348564B1

(12) United States Patent
Wautier et al.

(10) Patent No.: US 6,348,564 B1
(45) Date of Patent: Feb. 19, 2002

(54) CYCLIC ESTERKETONE COMPOUNDS, PROCESSES FOR THE SYNTHESIS THEREOF AND PROCESS FOR THE PREPARATION OF POLY (ESTERKETONE) POLYMERS

(75) Inventors: Henri Wautier, Braine-le-Comte; Jean-Pierre Latere, Liege; Philippe Lecomte, Cointe; Robert Jerome, Sart-Jalhay; Philippe Dubois, Ciplet, all of (BE)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 09/595,030

(22) Filed: Jun. 16, 2000

(30) Foreign Application Priority Data

Jun. 17, 1999 (EP) ............................. 99201957

(51) Int. Cl.[7] .............................. C08G 63/08
(52) U.S. Cl. ..................... 528/354; 528/220; 528/227; 528/486; 525/415

(58) Field of Search ................................. 528/354, 220, 528/227, 486, 415

(56) References Cited

U.S. PATENT DOCUMENTS 3,418,290 A 12/1968 Bantjes

OTHER PUBLICATIONS

Jmal Ouazzani–Chahdi, et al., "Preparation of Both Enantiomers of A Chiral Lactone Through Combined Microbiological Reduction And Oxidation," Tetrahedron Letters, vol. 28, No. 10, (1987), pp. 1109–1112.

*Primary Examiner*—Duc Truong
(74) *Attorney, Agent, or Firm*—Oblon, Spivak, McClelland, Maier & Neustadt, P.C.

(57) ABSTRACT

Unsubstituted oxepane-diones useful as monomers for the production of polymers, process for the synthesis thereof by oxidation of unsubstituted cyclohexanediones, process for the preparation of polyesterketone polymers by polymerization of cyclic esterketones and polyesterketone polymers so obtained.

13 Claims, No Drawings

CYCLIC ESTERKETONE COMPOUNDS, PROCESSES FOR THE SYNTHESIS THEREOF AND PROCESS FOR THE PREPARATION OF POLY (ESTERKETONE) POLYMERS

The present invention relates to new cyclic esterketone compounds which are useful as monomers for the production of polymers, to a process for the synthesis thereof and to a process for the preparation of poly(esterketone) polymers and to the poly(esterketone) polymers so obtained therewith.

In recent years there has been a strong preoccupation with the development of biodegradable and nontoxic polymers which may be used for replacing existing polymers. To be useful for such purposes, the polymers must also possess other properties of the polymers which they are intended to replace. Such properties include, inter alia, permeability, biocompatibility, promotion of bioadhesion and reactivity for attachment to drugs.

In this regard, various aliphatic polyesters derived from lactones have drawn interest. Of particular interest in this regard are those aliphatic polyesters derived from lactones and, in particular, those derived from ε-caprolactone. Polymers derived from ε-caprolactone (such polymers being referred to herein as Pε-CL) are one of the very few commercially available biodegradable polymers, being well known for its biocompatibility, permeability and biodegradability. Pε-CL also possesses the rare property of being miscible with a variety of other polymers (such as PVC), thereby permitting them to be formed therewith into polymer blends/alloys (e.g., copolymers) in which deficient properties of the other polymer(s), such as poor stress/crack resistance, gloss and adhesion, are ameliorated.

Pε-CL has been as particularly desirable for the replacement of certain polymers, vinylic and otherwise in plastic bags and in films and wrappings. Unfortunately, due to a relatively low melting point of about 60° C., the ability for Pε-CL to be employed to replace such polymers in such uses is extremely limited, with an increase of at least 20° C. being necessary.

To resolve the above-mentioned problems, a new polymer, (2-oxep ane-1,5-dione(also known, and referred to herein, as PKCL) has been synthesized which possesses a melting point of about 150° C. and a glass transition temperature of about 41° C. This polymer, is formed from the monomer 1,4,8-trioxaspiro[4,6-]-9-undecanone (also known as TOSUO) in a well-controlled "living" ring-opening polymerization reaction using aluminum isopropoxide [Al(OiPr)$_3$] as an initiator, whereby polyTOSUO is formed, followed by a reaction for 1 hour at 25° C. using Ph$_3$CBF$_4$ and CH$_2$Cl$_2$, whereby PKCL is formed.

TOSUO is, in turn, synthesized according to a Baeyer-Villiger reaction by the oxidation of 1,4-cyclohexanedione monoethylene acetal by 3-chloroperoxybenzoic acid (m-CPBA) at 40° C. in CH$_2$Cl$_2$. Unfortunately, the synthesis of TOSUO follows a pathway that requires separate steps, the first wherein the finctions of the ketone are shielded and the second wherein the acetal functions are deshielded, thereby complicating and increasing the cost and time required for the synthesis.

Accordingly, it can be seen that there remains a need to provide improved compounds which are useful as new monomers that may be polymerized to form poly (esterketone) polymers, which monomer compounds may also be directly synthesized from the starting material in high yield using a one-step process. It can further be seen that there remains a need to provide a process to form poly(esterketone) polymers from the monomer compounds, as well as a need to provide the poly(esterketone) polymers so obtained.

It is a first primary object of the present invention to provide new cyclic esterketone compounds which are useful as new monomers that may be polymerized to form poly (esterketones), in particular poly(oxepane-diones), more particularly poly(unsubstituted oxepane-diones) such as poly(2-oxepane-1,5-dione) (PKCL), so that said compounds may be used to replace TOSUO for use in producing PKCL.

It is a further object of the present invention to provide such a compound which may be easily obtained from the starting material in one-step.

It is a second primary object of the present invention to provide a process whereby the cyclic esterketone compounds of the present invention may be produced from the starting material in one-step.

It is a third primary object of the present invention to provide improved poly(esterketone) polymers.

It is a fourth primary object of the present invention, to provide a process for the preparation of poly(esterketone) polymers.

In accordance with the teachings of the present invention, disclosed herein are novel cyclic esterketone compounds which are useful as monomers for the production of poly(esterketone) polymers, in particular polyoxepane-diones, more particularly poly(unsubstituted oxepane-diones) such as poly(2-oxepane-1,5-dione) (PKCL). These compounds are also simple and easy to synthesize from their starting materials in high yield using a one-step process that involves the oxidation (and, particularly, mono-oxidation) of the starting material (and particularly, cyclic diketones, such as saturated cyclic diketones, more particularly cyclohexanediones, such as unsubstituted cyclohexanediones, for example 1,4-cyclohexanedione).

More precisely, disclosed herein are novel cyclic esterketones that are useful as monomers in the production of, e.g., PKCL. Preferably, these cyclic esterketones are chosen from appropriate oxepane-diones, namely unsubstituted oxepane-diones. Most preferred unsubstituted oxepane-dione is 2-oxepane-1,5-dione (referred to herein as KCL).

Unsubstituted oxepane diones particularly KCL) are particularly attractive compounds for use as monomers due to, inter alia, their long-term stability which translates into a good shelf life. In this regard, unsubstituted oxepane diones (particularly KCL) have a shelf-life, in open air at ambient temperature, of at least three months. Further, they may be conserved without substantial degradation for more than three months at −20° C., in an inert nitrogen atmosphere. Such long-term stability is important in the measure where these compounds may be prepared in large quantities, with all the benefits that are derived from such an economy of scale.

Unsubstituted oxepane diones (particularly KCL) are further particularly useful due to the ease by which they may be synthesized in a one-step reaction by oxidation of the starting material.

In another aspect of the present invention, disclosed herein is a process for the synthesis of the novel cyclic esterketone compounds of the present invention, and in particular of 2-oxepane-1,5-dione (KCL), that permits the compound to be easily and simply prepared directly from the starting material in one, step.

The process of the present invention for the synthesis of unsubstituted oxepane diones (particularly of KCL) permits these (monomer) compounds to be easily and simply prepared in one-step directly from the starting material. In other words, the (monomer) compounds of the present invention (more particularly, 2-oxepane-1,5-dione) are obtainable by this process of the present invention.

In particular, the process of the present invention involves the oxidation (e.g., mono-oxidation) of cyclic diketones (to esters) to produce cyclic esterketone monomers according to the invention. Preferably, these cyclic diketones are saturated cyclic diketones. Cyclohexanediones are specially recommended such as unsubstituted cyclohexanediones. Most preferred is 1,4-cyclohexanedione (which is used to synthesize KCL).

As will be readily understood (and as is capable of being determined) by one skilled in the art, the precise concentration of the starting material to be employed in the process of the present invention may be varied as needed to obtain the precise quantities of the (monomer) compounds of the present invention desired.

Nonetheless, it is contemplated herein that at least 0.01 M of starting material will be employed in the process of the present invention. Preferably, at least 0.06 M of starting material will be employed in the process of the present invention. Also preferred is the use of at least about 0.14 M of starting material. Still further preferred is the use of at least about 0.17 M of starting material. Most preferred is the use of at least about 0.2 M of starting material. In this regard, use of concentrations of 0.33 M, 0.55 M, 0.85 M and 0.99 M of starting material in the process of the present invention are particularly preferred.

As used herein, the symbol "M", when referring to concentrations (of, e.g., starting material, oxidant, catalysts, initiators, etc.), is used to stand for molarity (moles of the substance per liter of the solution).

Preferably, the cyclic diketones useful in the present invention are oxidized (mono-oxidized) (to esters) by an oxidant that is, preferably, a peracid. This is especially the case where 1,4-cyclohexanedione is the cyclic diketone and the compound (i.e., monomer) desired to be obtained is 2-oxepane-1,5-dione (KCL).

In this regard, it is preferred that the peracid is a perbenzoic acid or a chloroperacid. Particularly preferred in this regard is that the chloroperacid is chloroperbenzoic acid. Most preferred is that the chloroperbenzoic acid is meta-chloroperbenzoic acid.

The precise peracid chosen may be any which is suitable for the task as can be determined by one skilled in the art. However, it is contemplated herein that where 1,4-cyclohexanedione is used to synthesize KCL, use of a meta-chloroperbenzoic acid is most preferred.

It is contemplated herein that the oxidant to be used to oxidize (mono-oxidized) the starting material may be generated "in-situ". This is particularly the case when the oxidant is a peracid.

In order to generate the oxidant (e.g., peracid) "in-situ", it is contemplated herein that an aldehyde will be provided which will be reacted (in-situ) with oxygen ($O_2$).

An example of such an instance is addition of benzaldehyde (PhCHO) and oxygen to the starting material. In such a case, the oxygen reacts with the benzaldehyde to generate the peracid oxidant (perbenzoic acid) which then oxidizes the starting material. Another example is the addition of either a para-, ortho- or meta-chlorobenzaldehyde and oxygen to the starting material to generate, respectively, para-, ortho- or meta-chloroperbenzoic acid.

In such cases, the aldehyde is added as such and the oxygen is bubbled into the reaction medium by the use of any known apparatus which are well-known and used in the art for such a purpose.

As will be readily understood (and as is capable of being determined) by one skilled in the art, the precise concentration of the peracid or, in the event that "in-situ" generation of the peracid is desired), the aldehyde and the oxygen to be employed in the process herein varies depending upon the precise starting material, peracid, etc., which is used.

Nonetheless, it is contemplated herein that for every mole/liter (M) of starting material employed in this process, at least 1 mole/liter (M) of peracid will also be employed. Preferably, at least 1.1 M of peracid will be employed for every 1.0 M of starting material employed in the process of the present invention. Further preferred is the use of at least about 2.0 M of peracid will be employed for every 1.0 M of starting material. Still further preferred is the use of at least about 3.0 M of peracid will be employed for every 1.0 M of starting material.

It is further preferred that no more than about 3.0 M of peracid for every 1.0 M of the starting material be used in the process of the present invention.

In the process for the synthesis of the novel monomer compounds of the present invention, the precise conditions and times under which the, oxidation of the starting material is performed may be optimized according to the starting material used, the monomer compound desired and/or the concentrations thereof, as may be determined by one skilled in the art.

Nonetheless, as to time, it is contemplated herein that oxidation of the starting material will be. carried out for at least about 10 minutes. It is further contemplated herein that oxidation of the starting material will be carried out for up to about 48 hours. However, it should be understood that, if desired or needed, the process may be carried out for periods of less than 10 minutes and/or for more than 48 hours.

As to temperature, it is contemplated herein that oxidation of the starting material will be carried out at a temperature of at least about 0° C. It is further contemplated herein that oxidation of the starting material will be carried out in temperatures of up to about 120° C. However, it should be understood that, if desired or needed, the process may be carried out in temperatures of less than 0° C. and/or more than 120° C.

It is contemplated that the preferred operating conditions will be to carry out oxidation of the starting material for about 1 hour to about 24 hours at a temperature in the range of about 20° C. to about 80° C. Particularly preferred is to carry out oxidation of the starting material at about 40° C.

It is further preferred that oxidation of the cyclic diketones to form the monomer compounds according to the process of the present invention be carried out in the presence of a solvent. The solvent which is chosen for the synthesis of the monomers of the present invention may also be anyone which is suitable for the task as can be determined by one skilled in the art. Particularly preferred in this regard are dichloromethane and 1,2-dichloroethane.

Finally, it is noted that it is preferred that the oxidation of the cyclic diketones, and in particular of the unsubstituted cyclohexanediones (more preferably the 1,4-cyclohexanedione), according to the process of the present invention be done under the action of a catalyst. Examples of catalysts which would be useful in this regard are $Ni(acac)_2$, $Ni(dmp)_2$ which stands for bis-(dipivaloylmethanota)nickel (II) (ref: Yamada, T.; Takahashi, K.; Kato, K.; Takai, T.; Inoki, S.; Mukaiyama, T. Chem. Lett. 1991, 641), $Ni(OAc)_2$, $Cu(OAc)_2$ (ref: Bolm, C.; Schlingloff, G.; Weickhardt, K. Tetrahedron Lett. 1993, 34, 3405), heteropolyoxometalates (ref: Hamamoto, M.; Nakayama, K.; Nishiyama, Y.; Ishii, Y. *J. Org. Chem.* 1993, 58, 6421), iron (III) oxide, cobalt(p) oxide (ref: Li, X.; Wang, F.; Zhang, H.; Wang, C.; Song, G. *Synth. Commun.* 1996, 26, 1613). I this regard, it is preferred that the catatyst be iron (III) oxide.

The precise catalyst(s) to use and the precise concentration thereof to employ in the process of the present invention will vary depending upon various factors as will be readily understood by one skilled in the art.

In still another aspect of the present invention, disclosed herein is a (polymerization) process for the preparation of polymers, and in particular of polyesterketones, such as poly(oxepane-diones), preferably poly(unsubstituted oxepane-diones) and more preferably PKCL which can be used to replace Pϵ-CL. This process is characterized by the polymerization of cyclic esterketone compounds, in particular of oxepane-diones, most particularly of the unsubstituted oxepane-diones of the present invention, and most particularly of 2-oxepane-1,5-dione.

This process may be either a solution polymerization process or a mass polymerization process, as desired and as can be readily decided on and determined by those skilled in the art.

In the polymerization process of the present invention, the polymerization of the cyclic esterketone (particularly the oxepane-dione, such as an unsubstituted oxepane-dione, in particular, of 2-oxepane-1,5-dione), can be promoted by any type of initiator known in the art. Particularly attractive are metal alkoxides, the metal of which contains free p, d or f orbital of a favorable energy, e.g., Mg, Ti, Zr, Zn, Sn, Al, Y, La, Hf and rare earth atoms, such as Sm.

Preferably, aluminum isopropoxide [Al(OiPr)$_3$] is employed as an initiator in the polymerization process of the present invention.

As will be readily understood (and as is capable of being determined) by one skilled in the art, the precise concentration of the initiator to be employed in the process of the present invention may be varied as needed to obtain the polymer(s) which is (are) desired to be obtained thereby. In this regard, the concentration of the initiator to employ is defined by the molecular mass which is desired to be possessed by the polymer obtained therefrom.

In the polymerization process of the present invention, the polymerization can be promoted by any type of catalyst known in the art. Particularly attractive are metal oxides, halides or carboxylates, the metal of which contain free p, d or f orbital of a favorable energy, e.g., Mg, Ti, Zr, Zn, Sn, Al, Y, La, Hf and rare earth atoms, such as Sm. in the presence of protic species, such as alcohols, amines, thiols and water.

It is further preferred that such polymerization process employes Sn[OC(O)—CH(CH$_2$—CH$_3$)—(CH$_2$)$_3$—CH$_3$]$_2$ (herein referred to as stannous octoate) as a catalyst.

As will be readily understood (and as is capable of being determined) by one skilled in the art, the precise concentration of the catalyst to be employed in the process of the present invention may be-varied as needed to obtain the polymer(s) which is (are) desired to be obtained thereby.

It is further contemplated herein that in the polymerization process of the present invention, the polymerization may further be promoted by the use of any type of the aforementioned catalysts/initiators both in solution with apolar to medium polarity solvents, and in bulk (without any solvent).

The precise operating conditions and times to employ in the polymerization process of the present invention may be readily determined and optimized by one skilled in the art according to the process employed, the concentration of the starting material employed therein, the polymer desired and/or the quantities thereof.

Nonetheless, it is contemplated herein that the polymerization process of the present invention, be done at a temperature which is at least 0° C. It is further contemplated herein that the polymerization be done at a temperature which is at least 20° C. Further in this regard, it is also contemplated herein that the polymerization be done at a temperature of up to about 180° C. It is further contemplated herein that the polymerization be done at a temperature of up to about 120° C.

However, as will be readily understood by one skilled in the art, it should be understood that, if desired or needed, the polymerization process of the present invention may be carried out at temperatures of less than about 0° C. and/or at temperatures of greater than about 180° C.

In yet another aspect of the present invention, disclosed herein is a poly(esterketone) polymer which is obtainable by (and which has been obtained by) the polymerization process of the present invention.

The poly(esterketone) polymers according to the present invention, particularly poly(oxepane-dione) polymers such as poly(unsubstituted oxepane-dione) polymers, preferably PKCL are particularly useful polymers for replacing, in particular, PVC in films, wrapping and garbage bags. In this regard, it is noted that these poly(esterketone) polymers have a melting point of about 156° C. and a glass transition temperature of about 41° C. Accordingly, these polymers may be used in wide variety of applications in which Pϵ-CL, due to it's low melting point (about 60° C.) cannot.

Unless specifically otherwise stated, as used herein, the terms "polymer" and "polymer resin" are used to refer to and include homopolymers, copolymers, terpolymers, etc., and blends and alloys thereof.

Unless specifically otherwise stated, as used herein, the term "copolymer" refers to those polymers which are formed from two different monomers and includes block, graft, random and alternating polymers and blends and alloys thereof. In this regard, the polymer which comprised the copolymer may be either formed together, such as when at least two different types of monomers are polymerized at the same time and in the same reactor (commonly referred to as copolymerization) or they may be formed separately and mixed together either with or without reactivity therebetween.

If desired, the poly(esterketone) polymers of the present invention may be formed as copolymers (including but not limited to terpolymers) by either polymerization with at least one other monomer or by mixing (with or without chemical reactivity therebetween) of polymers which have been synthesized individually (e.g. by mixing in the presence of a transesterification catalyst, such as dibutyl tin oxide). Preferred poly(esterketone) copolymers of the invention are copolymers of KCL with at least one other monomer. Preferably, the at least one other monomer includes ϵ-CL. Other types of monomers/polymers which may be combined with KCL (either with random or sequential comonomer distribution) include but are not limited to lactides, glycolides, β-, γ-, δ- and ϵ-lactones, substituted or not and their polymers.

In this regard, copolymers of KCL and ϵ-CL are particularly contemplated as being preferred.

Preferably, such PKCL-ϵ-CL) copolymers have at least about 1% (w/w) KCL. More preferred is that such P(KCL-ϵ-CL) copolymers have at least about 5% (w/w) KCL. Most preferred in this regard is that such P(KCL-ϵ-CL) copolymers have at least about 8% (w/w) KCL.

Further preferred is that such PKCL-ε-CL) copolymers have no more than about 99% (w/w) KCL. More preferred is that such PQ(CL-ε-CL) copolymers have no more than about 80% (w/w) KCL. Most preferred in this regard is that such P(KCL-ε-CL) copolymers have no more than about 50% (w/w) KCL.

The PKCL copolymers according to the invention [particularly the P(KCL-ε-CL) random copolymers] provided for by the process of the present invention have both a high melting point (ranging from about 80° C. to about 150° C.) and a low glass transition temperature (ranging from about −20° C. to about 35° C.).

Having thus described the novel cyclic esterketone (monomer) compounds of the present invention, the process for the synthesis thereof, the poly(esterketone) polymers of the present invention and the process for the preparation thereof, the following examples are now presented for illustrative purposes only and are not meant to limit the scope of the invention.

EXAMPLE 1
Synthesis of KCL Monomer Compound

A sample of KCL monomer was prepared as follows.

Into a two-neck glass reactor equipped with a septum and a three-way stop cock and a coolingjacket on which is mounted a gas-exhaust valve the following was added: 0.17 M of 1,4-cyclohexanedione (98% by weight) (ALDRICH), 0.5 M of benzaldehyde (99% by weight, distilled before use) (ALDRICH), 0.001667 M of $Fe_2O_3$ (99.999% by weight, 100 mesh) (ACROS) and 60 ml of 1,2-dichloroethane (J. T. BAKER 8042) (assay (GC) minimum 99.5% w/w) which had been dried over molecular sieves (4 Å) (ALDRICH) just before use.

The reactor was then placed under magnetic agitation in an oil bath at 40° C. for 6 hours with oxygen bubbled into the reaction medium through a capillary tube, so as to saturate the solution.

After the six hour period, the oxygen bubbling was ceased and the temperature in the reactor Was permitted to drop to 20° C. before opening.

After evaporation of the solvent under reduced pressure, using a rotary film evaporatory (BUCHI water bath B-480), the precipitate was recovered.

The recovered crude product was then analyzed and the conversion to 2-oxepane-1,5-dione was determined by $^1$H-NMR.

$^1$H-NMR spectra of the 2-oxepane-1,5-dione (KCL) obtained was recorded in $CDCl_3$ at 400 MHz in the FT mode with a Bruker AN400 superconducting magnetic system at 25° C.

The results of this analysis revealed that the precipitate contained 29% (w/w) of 1,4-cyclohexanedione and 71% (w/w) of KCL.

EXAMPLE 2
Synthesis of KCL Monomer Compound

Three further samples of KCL monomer were prepared with the same ingredients and according to the same process as described above in Example 1 with the sole exceptions being that in each sample : 0.17 M of 1,4-cyclohexanedione (herein sometimes referred to as "dione"); 150 ml of 1,2-dichloroethane was used; and that the reaction times were varied, as follows: in the first of these three additional samples (Sample 2A), the reaction was performed for 3 hours during which oxygen was added, in the second of these three additional samples (Sample 2B) the reaction was performed for 6 hours during which oxygen was added, and in the third of these three additional samples (Sample 2C) the reaction was performed for 16 hours during which oxygen was added.

In each sample, oxidation of dione was done at 40° C. in the presence of 150 ml $ClCH_2CH_2Cl$ and PhCHO/[dione]= 3/1; [dione]$_0$=0.17M.

Following reaction, the KCL produced thereby was then recovered and the quantity thereof determined by $^1$H-NMR as described above in Example 1. The results of these determinations are as follows:

TABLE 1

| Sample | Time (in hours) | Conversion into KCL |
| --- | --- | --- |
| Sample 2A | 3 | 10% |
| Sample 2B | 6 | 37% |
| Sample 2C | 16 | 75% |

The effect of the dione quantity placed in operation at the beginning of the reaction had been attributed to the bubbling therein of oxygen which limits the quantity of oxidant agent (perbenzoic acid) which is generated "in situ" (compare example 1 and 2B). A longer reaction time permits to increase the quantity of oxygen which is introduced into the reactor. However, the lactone concentration is thereof limited by its degradation into the reaction medium.

EXAMPLE 3
Synthesis of KCL Monomer Compound

Two further samples of KCL monomer were prepared as follows: meta-Chloroperbenzoic acid (m-CPBA) having a purity of 70–75% (in peracid) was obtained (ACROS). This m-CPBA was washed with a phosphate buffer (pH=7.5) until a filtrate having a pH=7.5 was obtained. The residual peracid was then dried under reduced pressure for 48 hours at ambient temperature. (Vogel's, Textbook of Practical Organic Chemistry, $5^{th}$ Edition, at page 457).

Analysis by gas chromatography revealed that this purified m-CPBA had a purity of greater than 99%. Gas chromatography was performed on a VARIAN STAR 3400 CX chramatograph equiped with a column DB5 of 30 m length (ID 032 mm, film 1 $\mu$m). m-CPBA was dissolved in dichloromethane.

0.06 M of 1,4-cyclohexanedione (98% by weight) (ALDRICH), and 0.715 M of the purified m-CPBA (ACROS) were placed in a 500 ml reactor. Thereafter, 200 ml of commercial dichloromethane (99.5% w/w) (ACROS), which had been dried over molecular sieves (ALDRICH) just before use was added to the reactor and the solution subjected to reflux for 16 hours at 40° C.

After evaporation of the solvent under reduced pressure, the precipitate was recovered, washed three times, each time with 250 ml of diethyl ether, filtered and dried under vacuum to a constant weight.

The recovered dried product was then weighted in order to calculate the yield of the 2-oxepane-1,5-dione (KCL) and the purity of the resulting KCL was determined by $^1$H-NMR.

$^1$H-NMR spectrum of the 2-oxepane-1,5-dione (KCL) obtained for determining purity was recorded in $CDCl_3$ at 400 MHz in the FT mode with a Bruker AN400 superconducting magnetic system at 25° C.

A yield of about 56% (moles in comparison to the number of moles of the dione starting material) was calculated for the 2-oxepane-1,5-dione and the analysis by $^1$H-NMR of the KCL product obtained, revealed a purity of the 2-oxepane-1,5-dione of about 90%.

EXAMPLE 4
Synthesis of KCL Monomer Compound

Six further samples of KCL monomer were prepared as follows: meta-Chloroperbenzoic acid (m-CPBA) having a purity of 70–75% (in peracid) was obtained (ACROS). This m-CPBA was washed with a phosphate buffer (pH=7.5) until a filtrate having a pH=7.5 was obtained. (Vogel's, Textbook of Practical Organic Chemistry, $5^{th}$ Edition, at page 457). The residual peracid was then dried under reduced pressure for 48 hours at ambient temperature.

For each sample, 19.8 mmol of 1,4-cyclohexanedione (98% by weight) (ALDRICH) and 22.6 mmol of the purified m-CPBA were placed in a 50 ml reactor. Thereafter, commercial dichloromethane (ACROS) (purity of minimum 99.5% by weight) which had been dried over molecular sieves (ALDRICH) just before use was added to the reactor in such a quantity to give the resulting solution of each sample the following concentrations of the 1,4-cyclohexanedione:

Sample 4A—0.14 M; Sample 4B—0.2 M; Sample 4C—0.33 ),; Sample 4D—0.55 M; Sample 4E—0.85 M; and Sample 4F—0.99 M.

Thereafter, the solution of each sample was subjected to reflux for 4 hours at 40° C.

After evaporation of the solvent under reduced pressure, the precipitate was recovered, washed three times, each time with 40 ml of diethyl ether, filtered and dried under vacuum to a constant weight.

The recovered dried product was then weighted in order to calculate the yield of the 2-oxepane-1,5-dione. The results of the yield are as follows;

TABLE 2

| Sample | Concentration | Yield |
|--------|---------------|-------|
| 4A | 0.14 M | 47% |
| 4B | 0.2 M | 54% |
| 4C | 0.33 M | 56% |
| 4D | 0.55 M | 60% |
| 4E | 0.85 M | 58% |
| 4F | 0.99 M | 58% |

EXAMPLE 5
Purification of KCL 7.42 grams of KCL obtained as described above in Example 3, was placed into a 2 liter two-neck glass reactor which had been preheated under vacuum.

1500 ml toluene (ACROS) (which had previously been dried by refluxing over $CaH_2$ and distilled under reduced pressure just before use) was then added to the reactor via a capillary tube.

Two grams of $CaH_2$ were then introduced under agitation in the nitrogen atmosphere and the solution maintained under vigorous stirring at ambient temperature for 16 hours.

The solution was then filtered through a PYREX filter element (porosity: 17–40 micron) under a nitrogen atmosphere and transferred to another two liter reactor which had been preconditioned by heating under reduced pressure.

The toluene (1000 ml) was then partially evaporated under a reduced pressure and thereafter recooled to 6° C. for one night and the KCL becomes insoluble.

After being decanted, the residual solvent was eliminated under nitrogen agitation via a capillary tube. The KCL recovered was then dried at ambient temperature and under reduced pressure for 24 hours and recovered.

The recovered dried product was then weighted in order to calculate the yield of the 2-oxepane-1,5-dione (KCL), the purity of the resulting KCL was determined by $^1$H-NMR and the melting point was determined using a capillary tube melting point apparatus (ELECTROTHERMAL 9100).

$^1$H-NMR spectrum of the 2-oxepane-1,5-dione (KCL) obtained for determining purity was recorded in $CDCl_3$ at 400 MHz in the FT mode with a Bruker AN400 superconducting magnetic system.

A yield of about 70% (weight in comparison to the weight of introduced KCl) was calculated for the 2-oxepane-1,5-dione and the analysis by $^1$H-NMR of the 2-oxepane-1,5-dione (KCL) product revealed a purity of greater than about 98%.

Further, a melting point of about 110–112° C. was determined for the KCL so obtained.

EXAMPLE 6
Long-term Stability of KCL Monomer

KCL monomer, synthesized as described above in Example 3, was dried under reduced pressure for 24 hours.

A sample of the KCL monomer thus obtained was stored at ambient temperature in an air atmosphere and in natural light for three months. Another sample of the KCL monomer thus obtained was then stored at −20° C. in nitrogen atmosphere for three months.

Following the storage period, each of the samples were analyzed by $^1$H-NMR as was described above in Example 3 and by gas chromatography as was also described above in Example 3. These analyses revealed no signs of degradation of the KCL monomer of either sample.

EXAMPLE 7
Homopolymerization of KCL

KCL, obtained as described in Example 1, was then polymerized in the presence of stannous octoate for producing PKCL.

A reaction tube equipped with a three-way stop cock and rubber septum on which was mounted a gas-exhaust valve was preconditioned three times (under vacuum with the aid of a Bunsen burner).

Thereafter, and under nitrogen atmosphere, the following was added to the reaction tube: 2.5 mmol of KCL obtained as described above in Example 1; 1 ml of 0.05 M $Sn(Oct)_2$ (TEGOKAT 129, TH.GOLDSMITH AG) obtained as provided by supplier in toluene (ACROS) (which had previously been dried by refluxing over $CaH_2$ and distilled under reduced pressure just before use) was then added to the reactor via a capillary tube.

The reaction tube was then maintained under stirring in an oil bath at about 100° C. After 16 hours the reaction was stopped. The polymer PKCL was recovered from the reaction milieu by filtration on paper and washed liberally with methanol. The polymer obtained in this manner was then dried under vacuum to a constant weight. The yield of PKCL (in relation to the weight of the monomer is of about 95%).

The PKCL obtained as described above was then characterized by $^1$H-NMR (as described above in Example 1), DSC (using a Dupont 910 Differential Scanning Calorimeter thermal analyzer calibrated with Indium and following the manufacturer's instructions) and thermogravimetric analysis (TGA) performed under nitrogen with a Dupont TGA 51 thermogravimetric analyzer (heating rate=10° C./minute).

DSC analysis revealed that the PKCL so obtained possessed a particularly high melting point ($T_M$) of about 156° C. ($\Delta H_m$=90 J/g) and a glass transition temperature ($T_g$ of about 32° C. TGA analysis revealed a 5% (w/w) loss at a temperature of about 198° C. The decomposition temperature was determined to be about 220° C.

EXAMPLE 8
Homopolymerization of KCL

In a reaction tube equipped with a three-way stop cock and rubber septum was introduced 0.8 grams of KCL, obtained as described above in Example 3. 1.25 ml of a 0.05 M solution of $Sn(Oct)_2$ (TEGOKAT 129, Th. Goldschmnidt AG) in toluene (which was previously dried on $CaH_2$ and distilled) were placed in the reaction tube. The toluene was then evaporated under reduced pressure.

The reaction tube was maintained under agitation in an oil bath maintained at 100° C. After 2 hours, the reaction was stopped. The PKCL was recovered by filtration on paper and washed liberally with methanol.

The polymer obtained in this manner was then dried under vacuum to a constant weight. The yield of PKCL (in relation to the weight of the monomer) is of about 98%. The PKCL obtained was found to possess a high melting point ($T_M$) of about 156° C. and a glass transition temperature ($T_g$ of about 35° C.

EXAMPLE 9
Homopolymerization of the KCL

A reaction tube equipped with a three-way stop cock and rubber septum was preconditioned three times (under vacuum with the aid of a Bullsen burner).

Thereafter, and in nitrogen atmosphere, 0.6 grams of purified KCL, obtained as described above in Example 5, 0.1 ml of a 0.08 M solution of $Sn(Oct)_2$ (TEGOKAT 129, TH.GOLDSWTH AG) and 0.9 ml of toluene (ACROS) (which had previously been dried by refluxing over $CaH_2$ and distilled under reduced pressure just before use) was then added to the reactor via a capillary tube.

The reaction tube was maintained under agitation in an oil bath maintained at 90° C. After 6 hours, the reaction was stopped. The PKCL which had precipitated in the milieu was recovered by filtration on paper and washed liberally with methanol (LAB CBEMISTY 1340 assay: 99% by weight) as received from the supplier.

The polymer obtained in this manner was then dried under vacuum to a constant weight. The yield of PKCL (in relation to the weight of the monomer) is of about 90%.

EXAMPLE 10
Characterization of PKCL by Wide Angle X-ray Scattering (WAXS)

Samples of PKCL obtained using the TOSUO monomer (obtained as described in Macromolecules 1997, 30, 406–409) and using the PKCL polymer obtained as described above in Example 7, were analyzed by WAXS.

Powder WAXS diagrams were recorded with diffractometer having a Philips goniometer PW1050 equipped with a graphite monochromator located behind the receiving slit, a Philips generator PW 1130 (40 kV-20 mA, Ni-filtered Cu $K\alpha$ radiation at $\lambda$=1.5418 Å) and Philips Proportional Detector PW 1352.

The results of this analysis revealed that the PKCL produced starting from both monomers had three principle peaks with intensities relative to 100/40/10 were detected at 4.1, 3.4 and 2.8 Å, respectively, for the PKCL obtained starting from TOSUO and at 4.1, 3.4 and 2.8 Å, respectively, for the PKCL obtained starting from KCL.

EXAMPLE 11
Copolymerization with a-CL

KCL, obtained as described in Example 1, was then co-polymerized with $\epsilon$-CL in the presence of stannous octoate for 16 hours at 100° C. producing an P(KCL-$\epsilon$-CL) copolymer having KCL molar fraction of 0.29.

A reaction tube equipped with a three-way stop cock and rubber septum was preconditioned three times (under vacuum with the aid of a Bunsen burner).

Thereafter, under nitrogen atmosphere, 2 mmol of the KCL (obtained as described above in Example 1), 3.6 mmol of $\epsilon$-CL (ACROS) (which had been dried by refluxing over $CaH_2$ and distilled under reduced pressure just before use), 0.1 ml of a 0.05 M solution of $Sn(Oct)_2$ (TEGOKAT 129, TH.GOLDSMITH AG) in 0.9 ml of toluene (ACROS) (which had previously been dried by refluxing over $CaH_2$ and distilled under reduced pressure just before use) was then added to the reactor via a capillary tube, so that the KCL molar fraction fKcL in the comonomer feed equals 0.36.

The reaction tube was the maintained under stirring in an oil bath at about 100° C. After 16 hours the reaction was stopped. The copolymer was recovered, from the reaction milieu by precipitation in methanol (LAB CHEMISTY 1340 assay: 99% by weight) as received from the supplier.

The polymer obtained in this manner was then dried under vacuum to a constant weight. The yield of (P(KCL-$\epsilon$-CL) (in relation to the weight of the monomers) is of about 92%.

The P(KCL-$\epsilon$-CL) obtained as described above was then characterized by $^1$H-NMR (as described above in Example 1), Size-exclusion Chromotography (SEC) (performed in THF by using Hewlett-Packard 1090 liquid chromatography equipped with a Hewlett-Packard 1037 A refractometer index detector and using the protocol described in Macromolecules, 1997, 30, 1947–1954), DSC (using a Dupont 910 Differential Scanning Calorimeter thermal analyzer calibrated with Indium and following the manufacturer's instructions) and thermogravimetric analysis (TGA) (performed under nitrogen with a Dupont TGA 51 thermogravimetric analyzer (heating rate=10° C./minute).

$^1$H-NMR revealed a KCL molar fraction CL in the copolymer of 0.29. The P(KCL-$\epsilon$-CL) copolymer was also found to have a number average molecular weight of about 5200 and a polydispersity index of 2.6, as determined by SEC. The P(KCL-$\epsilon$-CL) copolymer was further found to possess two melting points ($T_M$) of about 77° C. and about 90° C. and a glass transition temperature ($T_g$ of about 3° C., as measured by DSC.

EXAMPLE 12
Copolymerization with $\epsilon$-CL

A reaction tube equipped with a three-way stop cock and rubber septum was preconditioned three times (under vacuum with the aid of a Bunsen burner).

Thereafter, in nitrogen atmosphere, 0.32 grams of purified KCL (obtained as described above in Example 5) was added to the reaction tube. 0.52 grams of $\epsilon$-CL (ACROS) (which had been dried by refluxing over $CaH_2$ and distilled under reduced pressure just before use) was then added to the reaction tube via a hypodermic syringe which also had been preconditionned three times (under vacuum with the aid of a Bunsen burner).

Furthermore, 4.6 ml of a 0.003 M solution of $Sn(Oct)_2$ (TEGOKAT 129, TH.GOLDSMITH AG) in 0.9 ml of toluene (ACROS) (which had previously been dried by refluxing over $CaH_2$ and distilled under reduced pressure just before use) was then added to the reactor via a capillary tube was then added to the reaction tube, also by hypodermic syringe.

The toluene was then evaporated under reduced pressure and the reaction tube maintained for four hours under agitation in an oil bath at 120° C. After 4 hours, the reaction was stopped. The viscous solution obtained was then diluted by 2 ml of tetrahydrofuran (99% by weight purity) (ACROS). The PKCL was then precipitated in 20 ml of cold methanol (LAB CBEMISTY 1340 assay: 99% by weight) as received from the supplier.

The polymer obtained in this manner was then dried under vacuum to a constant weight. The yield of P(KCL-ε-CL) (in relation to the weight of the monomers) is of about 84%.

EXAMPLE 13
Copolymerization with ε-CL

Three further P(KCL-a-CL) copolymers have been prepared as described above in Example 11 with the exception of the quantities of the KCL, ε-CL and Sn(Oct)$_2$ above which quantities are given in Table 3 below.

These copolymers were then recovered and analyzed, as was also described above in Example 12. The results of these analyses are given below in Table 3:

TABLE 3

| KCL quantity | εCL quantity | Sn(Oct)$_2$ 0.05M quantity | Yield | $F_{KCL}$ | Tg | Tm |
|---|---|---|---|---|---|---|
| 0.294 g | 0.3 ml | 1 ml | 85% | 0.41 | 6° C. | 78° C. and 94° C. |
| 0.183 g | 0.125 ml | 0.5 ml | 95% | 0.50 | 9° C. | 86° C. and 103° C. |
| 0.467 g | 0.15 ml | ml | 88% | 0.77 | 5° C. | 96° C. and 132° C. |

EXAMPLE 14
Copolymerization with ε-CL

A reaction tube equipped with a three-way stop cock and rubber septum was preconditioned three times (under vacuum with the aid of a Bunsen burner).

Thereafter, in nitrogen atmosphere, 0.06 grams of purified KCL (obtained as described above in Example 5) was added to the reaction tube. The KCL monomer was purified 3 times by azeotropic distillation with (3×7 ml) toluene (previously dried on CaH$_2$ and distilled under reduced pressure). 0.52 grams of ε-CL (ACROS), which had been previously dried on CaH$_2$ and distilled under reduced pressure, was then added to the reaction tube via a hypodermic syringe which also had been preconditionned three times (under nitrogen atmosphere) with the aid of a Bunsen burner).

3 ml of toluene (which was previously dried on CaH$_2$ and distilled) were placed in the reaction tube which was maintained for 10 minutes under agitation in an oil bath at 90° C.

0.4 ml of a 0.11 M solution of Al(OiPr)$_3$, which had been previously twice sublimated and then dissolved in toluene (which was previously dried on CaH$_2$ and distilled) under nitrogen, was then added to the reaction tube, also by hypodermic syringe.

The reaction tube was maintained for four hours under agitation in an oil bath at 90° C. After 4 hours, the reaction was stopped. The viscous solution obtained was then diluted by 2 ml of tetrahydrofuran (ACROS). The copolymer was then precipitated in 20 ml of cold methanol (Lab Chemistry, 99%).

The polymer obtained in this manner was then dried under vacuum to a constant weight. The yield of the P(KCL-ε-CL) (in relation to the weight of the monomers) is of about 97%.

EXAMPLE 15
Copolymerization with ε-CL

A reaction tube equipped with a three-way stop cock and rubber septum was preconditioned three times (under vacuum with the aid of a Bunsen burner).

Thereafter, in nitrogen atmosphere, 0.32 grams of purified KCL (obtained as described above in Example 5) was added to the reaction tube. 0.52 grams of ε-CL (ACROS) which had been previously dried on CaH$_2$ and distilled under reduced pressure, was then added to the reaction tube via a hypodermic syringe which also had been preconditionned three times (under vacuum with the aid of a Bunsen burner).

2 ml of a 0.003 M solution of Sn(Oct)$_2$ (TEGOKAT 129, Th. Goldschmidt AG) and 0.25 ml of a 0.06 M of 1-phenyl-2-propanol (SIGMA-ALDRICH; assay: 98%) in toluene (in both case toluene was previously dried on CaH$_2$ and distilled) were added to the reaction tube by hypodermic syringe.

The toluene was then evaporated under reduced pressure and the reaction tube maintained for one hour under agitation in an oil bath at 120° C. After 4 hours, the reaction was stopped. The viscous solution obtained was then diluted by 2 ml of tetrahydrofuran (ACROS). The copolymer was then precipitated in 20 ml of cold methanol (Lab Chemistry, 99%).).

The polymer obtained in this manner was then dried under vacuum to a constant weight. The yield of the PKCL-ε-CL) (in relation to the weight of the monomers) is of about 84%.

While specific embodiments of the present invention have been shown and described to illustrate the inventive principles herein, it is to be understood that this is only meant to be illustrative and not limiting of the invention disclosed herein.

What is claimed is:

1. A cyclic esterketone, which is an unsubstituted oxepane-dione.

2. The cyclic esterketone according to claim 1, which is 2-oxepane-1,5-dione.

3. A process of synthesizing a monomer compound comprising oxidation of an unsubstituted cyclohexanedione.

4. The process according to claim 3, wherein the unsubstituted cyclohexanedione is 1,4-cyclohexanedione.

5. The process according to claim 3, wherein a peracid or an aldehyde is used for the oxidation of the unsubstituted cyclohexanedione.

6. The process according to claim 5, wherein the peracid is perbenzoic acid or a chloroperacid.

7. The process according to claim 6, wherein the chloroperacid is a meta-chloroperbenzoic acid.

8. A process for the preparation of a poly(esterketone) polymer comprising polymerization of a cyclic esterketone, which is an unsubstituted oxepane-dione.

9. A process according to claim 8, wherein the unsubstituted oxepane-dione is 2-oxepane-1,5-dione.

10. A poly(esterketone) polymer obtained by the polymerization process of claim 8.

11. Polymer according to claim 10 obtained by copolymerization of 2-oxepane-1,5-dione with at least one other monomer.

12. Polymer according to claim 11 wherein the at least one other monomer includes ε-CL.

13. Polymer according to claim 11 which comprises from about 5% to about 80% (w/w) KCL.

* * * * *